(12) United States Patent
Weber et al.

(10) Patent No.: US 8,802,842 B2
(45) Date of Patent: Aug. 12, 2014

(54) METHOD FOR THE PREPARATION OF A CRYSTALLINE FORM

(75) Inventors: Dirk Weber, Mainz (DE); Svenja Renner, Eckenroth (DE); Tobias Fiedler, Muenster-Sarmsheim (DE); Simone Orlich, Schoneberg (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 12/892,310

(22) Filed: Sep. 28, 2010

(65) Prior Publication Data

US 2011/0237526 A1    Sep. 29, 2011

(30) Foreign Application Priority Data

Sep. 30, 2009  (EP) ................................. 09171847

(51) Int. Cl.
| | |
|---|---|
| *C07H 1/06* | (2006.01) |
| *C07H 1/08* | (2006.01) |
| *C07H 15/203* | (2006.01) |
| *C07H 5/02* | (2006.01) |
| *A01N 43/04* | (2006.01) |
| *A61K 31/70* | (2006.01) |

(52) U.S. Cl.
CPC .................................... *C07H 15/203* (2013.01)
USPC ............................ 536/127; 536/122; 514/23

(58) Field of Classification Search
None
See application file for complete search history.

(56) References Cited

U.S. PATENT DOCUMENTS

| | | |
|---|---|---|
| 3,174,901 A | 3/1965 | Sterne |
| 3,884,906 A | 5/1975 | Van Der Meer et al. |
| 4,379,785 A | 4/1983 | Weyer et al. |
| 4,602,023 A | 7/1986 | Kiely et al. |
| 4,639,436 A | 1/1987 | Junge et al. |
| 4,786,023 A | 11/1988 | Harris et al. |
| 4,786,755 A | 11/1988 | Kiely et al. |
| 5,880,289 A | 3/1999 | Kaneko et al. |
| 6,414,126 B1 | 7/2002 | Ellsworth et al. |
| 6,515,117 B2 | 2/2003 | Ellsworth et al. |
| 6,613,806 B1 | 9/2003 | Aven et al. |
| 6,627,611 B2 | 9/2003 | Tomiyama et al. |
| 6,774,112 B2 | 8/2004 | Gougoutas |
| 6,794,480 B2 | 9/2004 | Goto et al. |
| 6,936,590 B2 | 8/2005 | Washburn et al. |
| 6,972,283 B2 | 12/2005 | Fujikura et al. |
| 7,169,761 B2 | 1/2007 | Tomiyama et al. |
| 7,202,350 B2 | 4/2007 | Imamura et al. |
| 7,371,732 B2 | 5/2008 | Eickelmann et al. |
| 7,375,087 B2 | 5/2008 | Teranishi et al. |
| 7,375,090 B2 | 5/2008 | Himmelsbach et al. |
| 7,375,213 B2 | 5/2008 | Deshpande et al. |
| 7,393,836 B2 | 7/2008 | Eckhardt et al. |
| 7,407,955 B2 | 8/2008 | Himmelsbach et al. |
| 7,417,032 B2 | 8/2008 | Eckhardt et al. |
| 7,419,959 B2 | 9/2008 | Eckhardt et al. |
| 7,541,341 B2 | 6/2009 | Fushimi et al. |
| 7,579,449 B2 | 8/2009 | Eckhardt et al. |
| 7,589,193 B2 | 9/2009 | Washburn et al. |
| 7,662,790 B2 | 2/2010 | Himmelsbach et al. |
| 7,674,486 B2 | 3/2010 | Bhaskaran et al. |
| 7,683,160 B2 | 3/2010 | Eckhardt et al. |
| 7,687,469 B2 | 3/2010 | Eckhardt et al. |
| 7,713,938 B2 | 5/2010 | Himmelsbach et al. |
| 7,723,309 B2 | 5/2010 | Himmelsbach et al. |
| 7,745,414 B2 | 6/2010 | Eckhardt et al. |
| 7,772,191 B2 | 8/2010 | Eckhardt et al. |
| 7,772,192 B2 | 8/2010 | Esko |
| 7,772,378 B2 | 8/2010 | Himmelsbach et al. |
| 7,772,407 B2 | 8/2010 | Imamura et al. |
| 7,776,830 B2 | 8/2010 | Eckhardt et al. |
| 7,847,074 B2 | 12/2010 | Eckhardt et al. |
| 7,851,502 B2 | 12/2010 | Bindra et al. |
| 7,851,602 B2 | 12/2010 | Himmelsbach et al. |
| 7,858,587 B2 | 12/2010 | Eckhardt et al. |
| 7,879,806 B2 | 2/2011 | Himmelsbach et al. |
| 7,879,807 B2 | 2/2011 | Himmelsbach et al. |
| 8,039,441 B2 | 10/2011 | Himmelsbach et al. |
| 8,119,648 B2 | 2/2012 | Himmelsbach et al. |
| 8,178,541 B2 | 5/2012 | Himmelsbach et al. |
| 8,232,281 B2 | 7/2012 | Dugi et al. |
| 8,283,326 B2 | 10/2012 | Eckhardt et al. |
| 8,507,450 B2 | 8/2013 | Eckhardt et al. |
| 8,551,957 B2 | 10/2013 | Dugi et al. |
| 8,557,782 B2 | 10/2013 | Eckhardt et al. |
| 2002/0137903 A1 | 9/2002 | Ellsworth et al. |

(Continued)

FOREIGN PATENT DOCUMENTS

| | | |
|---|---|---|
| CA | 2382480 A1 | 3/2001 |
| CA | 2388818 A1 | 4/2001 |

(Continued)

OTHER PUBLICATIONS

McMaster University, Chem2O06 Lab Manual, Aug. 1997, Expt. 1, Part B.*
Ault, Techniques and experiments for organic chemistry, University Science Books, 1998, pp. 59-60.*
Adachi, Tetsuya., et al; T-1095, A Renal Na+-E-Glucose Transporter Inhibitor, Improves Hyperglycemia in Streptozotocin-Induced Diabetic Rats; Metabolism (2000) vol. 49 No. 8 pp. 990-995.
Benhaddou, Rachida., et al; Tetra-n-Propylammonium Tetra-Oxoruthenate(VII): A Reagent of Choice for the Oxidation of Diversely Protected Glycopyranoses and Glycofuranoses to Lactones; Carbohydrate Research (1994) vol. 260 pp. 243-250.
Byrn, Stephen et al. "Pharmaceutical Solids: A Strategic Approach to Regulatory Considerations" Pharmaceutical Research, vol. 12, No. 7, (1995) pp. 945-954.

(Continued)

*Primary Examiner* — Layla Bland
(74) *Attorney, Agent, or Firm* — Michael P. Morris; Edouard G. Lebel

(57) ABSTRACT

The invention relates to a method for the preparation for a crystalline form of 1-chloro-4-(β-D-glucopyranos-1-yl)-2-[4-((S)-tetrahydrofuran-3-yloxy)-benzyl]-benzene. In addition the invention relates to a crystalline form obtainable by this method, to a pharmaceutical composition and to the use thereof for preparing medicaments.

13 Claims, 1 Drawing Sheet

(56) References Cited

U.S. PATENT DOCUMENTS

| | | |
|---|---|---|
| 2003/0064935 A1 | 4/2003 | Gougoutas |
| 2003/0087843 A1 | 5/2003 | Washburn |
| 2003/0114390 A1 | 6/2003 | Washburn et al. |
| 2004/0138148 A1 | 7/2004 | Fushimi et al. |
| 2004/0138439 A1 | 7/2004 | Deshpande et al. |
| 2005/0065098 A1 | 3/2005 | Fujikura et al. |
| 2005/0085680 A1 | 4/2005 | Auerbach et al. |
| 2005/0124555 A1 | 6/2005 | Tomiyama et al. |
| 2005/0187168 A1 | 8/2005 | Eickelmann et al. |
| 2005/0209166 A1 | 9/2005 | Eckhardt et al. |
| 2005/0233982 A1 | 10/2005 | Himmelsbach et al. |
| 2006/0009400 A1 | 1/2006 | Eckhardt et al. |
| 2006/0019948 A1 | 1/2006 | Eckhardt et al. |
| 2006/0025349 A1 | 2/2006 | Eckhardt et al. |
| 2006/0035841 A1 | 2/2006 | Eckhardt et al. |
| 2006/0063722 A1 | 3/2006 | Washburn et al. |
| 2006/0074031 A1 | 4/2006 | Eckhardt et al. |
| 2006/0142210 A1 | 6/2006 | Eckhardt et al. |
| 2006/0189548 A1 | 8/2006 | Himmelsbach et al. |
| 2006/0210627 A1 | 9/2006 | Pfeffer et al. |
| 2006/0234953 A1 | 10/2006 | Himmelsbach et al. |
| 2006/0251728 A1 | 11/2006 | Himmelsbach et al. |
| 2006/0258749 A1 | 11/2006 | Eckhardt et al. |
| 2007/0004648 A1 | 1/2007 | Himmelsbach et al. |
| 2007/0027092 A1 | 2/2007 | Himmelsbach et al. |
| 2007/0049537 A1 | 3/2007 | Eckhardt et al. |
| 2007/0054867 A1 | 3/2007 | Eckhardt et al. |
| 2007/0073046 A1 | 3/2007 | Eckhardt et al. |
| 2007/0249544 A1 | 10/2007 | Himmelsbach et al. |
| 2007/0259821 A1 | 11/2007 | Eckhardt et al. |
| 2007/0281940 A1 | 12/2007 | Dugi et al. |
| 2008/0058379 A1 | 3/2008 | Eckhardt et al. |
| 2008/0107731 A1 | 5/2008 | Kohlrausch et al. |
| 2008/0234367 A1 | 9/2008 | Washburn et al. |
| 2008/0287529 A1 | 11/2008 | Deshpande et al. |
| 2009/0023913 A1 | 1/2009 | Eckhardt et al. |
| 2009/0318547 A1 | 12/2009 | Eckhardt et al. |
| 2009/0326215 A1 | 12/2009 | Eckhardt et al. |
| 2010/0069310 A1 | 3/2010 | Himmelsbach et al. |
| 2010/0081625 A1 | 4/2010 | Wienrich et al. |
| 2010/0093654 A1 | 4/2010 | Himmelsbach et al. |
| 2010/0099641 A1 | 4/2010 | Himmelsbach et al. |
| 2010/0179191 A1 | 7/2010 | Himmelsbach et al. |
| 2010/0209506 A1 | 8/2010 | Eisenreich |
| 2010/0240879 A1 | 9/2010 | Eckhardt et al. |
| 2010/0249392 A1 | 9/2010 | Eckhardt et al. |
| 2010/0298243 A1 | 11/2010 | Manuchehri et al. |
| 2010/0317847 A1 | 12/2010 | Eckhardt et al. |
| 2011/0014284 A1 | 1/2011 | Eisenreich et al. |
| 2011/0046076 A1 | 2/2011 | Eickelmann et al. |
| 2011/0046087 A1 | 2/2011 | Eickelmann et al. |
| 2011/0065731 A1 | 3/2011 | Dugi et al. |
| 2011/0098240 A1 | 4/2011 | Dugi et al. |
| 2011/0178033 A1 | 7/2011 | Eckhardt et al. |
| 2011/0195917 A1 | 8/2011 | Dugi et al. |
| 2011/0206766 A1 | 8/2011 | Friedl et al. |
| 2011/0236477 A1 | 9/2011 | Schneider et al. |
| 2011/0237526 A1 | 9/2011 | Weber et al. |
| 2011/0237789 A1 | 9/2011 | Weber et al. |
| 2012/0071403 A1 | 3/2012 | Strumph et al. |
| 2012/0196812 A1 | 8/2012 | Eickelmann et al. |
| 2012/0219622 A1 | 8/2012 | Kohlrausch et al. |
| 2012/0296080 A1 | 11/2012 | Eckhardt et al. |
| 2013/0035821 A1 | 2/2013 | Bonne et al. |
| 2013/0064887 A1 | 3/2013 | Ito et al. |
| 2013/0096076 A1 | 4/2013 | Dugi et al. |
| 2013/0137646 A1 | 5/2013 | Wienrich et al. |
| 2013/0236543 A1 | 9/2013 | Ito et al. |
| 2013/0252908 A1 | 9/2013 | Mayoux et al. |
| 2014/0031301 A1 | 1/2014 | Eickelmann et al. |
| 2014/0038911 A1 | 2/2014 | Eickelmann et al. |
| 2014/0046046 A1 | 2/2014 | Eckhardt et al. |
| 2014/0087996 A1 | 3/2014 | Klein et al. |
| 2014/0088027 A1 | 3/2014 | Grempler et al. |

FOREIGN PATENT DOCUMENTS

| | | |
|---|---|---|
| CA | 2437240 A1 | 8/2002 |
| CA | 2494177 A1 | 2/2004 |
| CA | 2496249 A1 | 3/2004 |
| CA | 2470365 A1 | 6/2004 |
| CA | 2508024 A1 | 6/2004 |
| CA | 2508226 A1 | 6/2004 |
| CA | 2526145 A1 | 9/2004 |
| CA | 2539032 A1 | 3/2005 |
| CA | 2548353 A1 | 7/2005 |
| CA | 2557269 A1 | 9/2005 |
| CA | 2557320 A1 | 9/2005 |
| CA | 2557801 A1 | 10/2005 |
| CA | 2569915 A1 | 1/2006 |
| CA | 2572149 A1 | 1/2006 |
| CA | 2572819 A1 | 1/2006 |
| CA | 2573777 A1 | 2/2006 |
| CA | 2574451 A1 | 2/2006 |
| CA | 2574500 A1 | 4/2006 |
| CA | 2649922 A1 | 11/2007 |
| CA | 2651019 A1 | 11/2007 |
| CA | 2720450 A1 | 10/2009 |
| DE | 2758025 A1 | 7/1979 |
| DE | 2951135 A1 | 6/1981 |
| EP | 0206567 A2 | 12/1986 |
| EP | 1224195 B | 7/2002 |
| EP | 1344780 A1 | 9/2003 |
| EP | 1385856 A | 2/2004 |
| EP | 1553094 A1 | 7/2005 |
| EP | 1564210 A1 | 8/2005 |
| EP | 1609785 A1 | 12/2005 |
| EP | 1791852 A2 | 6/2007 |
| EP | 1852108 A1 | 11/2007 |
| JP | 55007256 A | 1/1980 |
| JP | 56039056 A | 4/1981 |
| JP | 58164502 | 9/1983 |
| JP | 62030750 A | 2/1987 |
| JP | H1085502 A | 4/1998 |
| JP | 11124392 A | 5/1999 |
| JP | 2001288178 A | 10/2001 |
| JP | 2003511458 A | 3/2003 |
| JP | 2004196788 A | 7/2004 |
| JP | 2004359630 | 12/2004 |
| JP | 2005002092 A | 1/2005 |
| JP | 2005060625 A | 3/2005 |
| WO | 9831697 A1 | 7/1998 |
| WO | 0116147 A1 | 3/2001 |
| WO | 0127128 A1 | 4/2001 |
| WO | 0174834 A1 | 10/2001 |
| WO | 02064606 A1 | 8/2002 |
| WO | 02083066 A2 | 10/2002 |
| WO | 03020737 A1 | 3/2003 |
| WO | 03031458 A1 | 4/2003 |
| WO | 03078404 A1 | 9/2003 |
| WO | 03099836 A1 | 12/2003 |
| WO | 2004007517 A1 | 1/2004 |
| WO | 2004013118 A1 | 2/2004 |
| WO | 2004018468 A2 | 3/2004 |
| WO | 2004046115 A1 | 6/2004 |
| WO | 2004052902 A1 | 6/2004 |
| WO | 2004052903 A1 | 6/2004 |
| WO | 2004063209 A2 | 7/2004 |
| WO | 2004076470 A2 | 9/2004 |
| WO | 2004080990 A1 | 9/2004 |
| WO | 2005012318 A2 | 2/2005 |
| WO | 2005012326 A1 | 2/2005 |
| WO | 2005021566 A2 | 3/2005 |
| WO | 2005063785 A2 | 7/2005 |
| WO | 2005085237 A1 | 9/2005 |
| WO | 2005085265 A1 | 9/2005 |
| WO | 2005092877 A1 | 10/2005 |
| WO | 2006002912 A1 | 1/2006 |
| WO | 2006006496 A1 | 1/2006 |
| WO | 2006008038 A1 | 1/2006 |
| WO | 2006010557 A1 | 2/2006 |
| WO | 2006011469 A1 | 2/2006 |
| WO | 2006018150 A1 | 2/2006 |
| WO | 2006034489 A2 | 3/2006 |

(56) References Cited

FOREIGN PATENT DOCUMENTS

| | | | |
|---|---|---|---|
| WO | 2006037537 | A2 | 4/2006 |
| WO | 2006064033 | A2 | 6/2006 |
| WO | 2006089872 | A1 | 8/2006 |
| WO | 2006108842 | A1 | 10/2006 |
| WO | 2006117359 | A1 | 11/2006 |
| WO | 2006117360 | A1 | 11/2006 |
| WO | 2006120208 | A1 | 11/2006 |
| WO | 2007000445 | A1 | 1/2007 |
| WO | 2007014894 | A2 | 2/2007 |
| WO | 2007025943 | A2 | 3/2007 |
| WO | 2007028814 | A1 | 3/2007 |
| WO | 2007031548 | A2 | 3/2007 |
| WO | 2007039417 | A1 | 4/2007 |
| WO | 2007093610 | A1 | 8/2007 |
| WO | 2007128724 | A1 | 11/2007 |
| WO | 2007128749 | A1 | 11/2007 |
| WO | 2007128761 | A2 | 11/2007 |
| WO | 2007144175 | A2 | 12/2007 |
| WO | 2008020011 | A1 | 2/2008 |
| WO | 2008034859 | A1 | 3/2008 |
| WO | 2008049923 | A1 | 5/2008 |
| WO | 2008055870 | A1 | 5/2008 |
| WO | 2008055940 | A2 | 5/2008 |
| WO | 2008062273 | A2 | 5/2008 |
| WO | 2008089892 | A1 | 7/2008 |
| WO | 2008090210 | A1 | 7/2008 |
| WO | 2008101938 | A1 | 8/2008 |
| WO | 2008101939 | A1 | 8/2008 |
| WO | 2008101943 | A1 | 8/2008 |
| WO | 2008116179 | A1 | 9/2008 |
| WO | 2008116195 | A2 | 9/2008 |
| WO | 2009022007 | A1 | 2/2009 |
| WO | 2009022010 | A1 | 2/2009 |
| WO | 2009035969 | A1 | 3/2009 |
| WO | 2009091082 | A1 | 7/2009 |
| WO | 2009121945 | A2 | 10/2009 |
| WO | 2010092123 | A1 | 8/2010 |
| WO | 2010092124 | A1 | 8/2010 |
| WO | 2010092125 | A1 | 8/2010 |
| WO | 2010092126 | A1 | 8/2010 |
| WO | 2010138535 | A1 | 12/2010 |
| WO | 2011039107 | A1 | 4/2011 |
| WO | 2011039108 | A2 | 4/2011 |
| WO | 2011039337 | A1 | 4/2011 |
| WO | 2011060290 | A2 | 5/2011 |
| WO | 2011120923 | A1 | 10/2011 |
| WO | 2012031124 | A2 | 3/2012 |
| WO | 2012062698 | A1 | 5/2012 |
| WO | 2012106303 | A1 | 8/2012 |
| WO | 2012107476 | A1 | 8/2012 |
| WO | 2012120040 | A1 | 9/2012 |

OTHER PUBLICATIONS

Deacon, Carolyn F. "Perspectives in Diabetes Therapeutic Strategies Based on Glucagon-Like Peptide 1" Diabetes, (2004) vol. 53 pp. 2181-2189.

Diabetes Mellitus, Merck Manual Online Edition, (retrieved Sep. 13, 2011) http://www.merckmanuals.com/professional/endocrine_and_metabolic_disorders/diabetes_mellitus_and_disorders_of_carbohydrate_metabolism/diabetes_mellitus_dm.html#v987998. Revision Jun. 2008.

Dohle, Wolfgang., et al; Copper-Mediated Cross-Coupling of Functionalized Arylmagnesium Reagents with Functionalized Alkyl and Benzylic Halides; Organic Letters (2001) vol. 3 No. 18 pp. 2871-2873.

Drug Watch "Type 2 Diabetes Mellitus" Formulary vol. 43 Aug. 2008 p. 304.

Fuerstner, Alois., et al; Practical Method for the Rhodium-Catalyzed Addition of Aryl- and Alkenylboronic Acids to Aldehydes; Advanced Synthesis and Catalysis (2001) vol. 343 No. 4 pp. 343-350.

Fujimori, Yoshikazu et al. "Remogliflozin Etabonate in a Novel Category of Selective Low-Affinity Sodium Glucose Cotransporter (SGLT2) Inhibitors, Exhibits Antidiabetic Efficacy in Rodent Models" (2008) Journal of Pharmacology and Experimental Therapeutics vol. 327 No. 1, pp. 268-276.

Ghassemi et al. "Synthesis and properties of new sulfonated poly(p-phenylene) derivatives for proton exchange membranes" Polymer (2004) pp. 5847-5854.

Greco, Gary T. et al. "Segregation of Active Constituents from Tablet Formulations During Grinding: Theoretical Considerations" Drug Development and Industrial Pharmacy, (1982) 8(4), pp. 565-578.

Hatsuda, Asanori., et al; A Practical Synthesis of Highly Functionalized Aryl Nitriles Through Cyanation of Aryl Bromides Employing Heterogeneous Pd/C; Tetrahedron Letters (2005) vol. 46 pp. 1849-1853; Elsevier Ltd.

Hussey, Elizabeth K. et al. "Safety, Pharmacokinetics and Pharmacodynamics of Remogliflozin Etabonate (SGLT2 Inhibitor) and Metformin When Co-Administered in Type 2 Diabetes Mellitus (T2DM) Patients" Diabetes, American Diabetes Association, (2009) XP00913667, vol. 58, p. A157.

Hutton, Craig A., et al; A Convenient Preparation of dityrosine Via Miyaura Borylation-Suzuki Coupling of Iodotyrosine Derivatives; Tetrahedron Letters (2003) vol. 44 pp. 4895-4898; Pergamon Press.

Iida, Takehiko., et al; Tributylmagnesium Ate Complex-Mediated Novel Bromine-Magnesium Exchange Reaction for Selective Monosubstitution of Dibromoarenes; Tetrahedron Letters (2001) vol. 42 pp. 4841-4844; Pergamon Press.

International Search Report for PCT/EP2005/002618 mailed Jun. 30, 2005.

International Search Report for PCT/EP2006/061956 mailed on Jul. 5, 2006.

International Search Report for PCT/EP2006/062191 mailed Aug. 8, 2006.

International Search Report for PCT/EP2010//064117 mailed on Nov. 30, 2010.

International Search Report for PCT/EP2010/064120 mailed Mar. 31, 2011.

Isaji, Masayuki "Sodium-glucose cotransporter inhibitors for diabetes" Current Opinion in Investigational Drugs, (2007) vol. 8, No. 4, pp. 285-292.

Jagdmann Jr, G. Erik ; Synthesis of 5-(4-Substituted Benzyl)-2,4-Diaminoquinazolines as Inhibitors of *Candida albicans* Dihydrofolate Reductase; Journal Heterocyclic Chemical (1995) vol. 32 pp. 1461-1465.

Kadowaki, T et al. "PPAR gamma agonist and antagonist" Nihon Yakurigaku Zasshi (2001) vol. 118, No. 9, pp. 321-326. (English abstract).

Knochel, Paul et al. "Highly functionalized Organomagnesium Reagents Prepared through Halogen-Metal Exchange" Angew. Chem. INt. Ed. (2003) vol. 42, 4302-4320.

Koo, Ja Seo., et al; 2-Pyridyl Cyanate: A Useful Reagent for he Preparation of Nitriles; Synthetic Communications (1996) vol. 26 No. 20 pp. 3709-3713; Marcel Dekker, Inc.

Krasovskiy Arkady et al. "A LiCL-Mediated Br/Mg Exchange Reaction for the Preparation of Functionalized Aryl- and Heterarylmagnesium Compounds from Organic Bromides" Angew. Chem. Int. Ed. (2004) vol. 43, pp. 3333-3336.

Kuribayashi, Takeshi., et al; Bis C-Glycosylated Diphenylmethanes for Stable Glycoepitope Mimetics; Syntletters (1999) vol. 6 pp. 737-740.

Kuribayashi, Takeshi., et al; c-Glycosylated Aryl tins: Versatile Building Blocks for Aryl C-Glycoside Glycomimetics; J. Carbohydrate Chemistry (1999) vol. 18, No. 4 pp. 371-382.

Kuribayashi, Takeshi., et al; C-Glycosylated Diphenylmethanes and Benzophenones: The Stille Coupling Reaction of C-Glycosylated Aryl tins with Benzyl Bromides and Acid Chlorides; J. Carbohydrate Chemistry (1999) vol. 18, No. 4 pp. 393-401.

Langle, Sandrine., et al; Selective Double Suzuki Cross-Coupling Reactions. Synthesis of Unsymmetrical Diaryl (or Heteroaryl) Methanes; Tetrahedron Letters (2003) vol. 44 pp. 9255-9258; Pergamon Press.

Lehmann, Ule et al. "Palladium-Catalyzed Cross-Coupling Reactions between Dihydropyranylindium Reagents and Aryl Halides, Synthesis of C-Aryl Glycals" Organic Letters, 2003, vol. 5, No. 14, pp. 2405-2408.

(56) References Cited

OTHER PUBLICATIONS

Li, T, et al. "Lack of Pharmacokinetic Interaction between Dapagliflozin and Pioglitazone in Healthy Subjects" Journal of Clinical Pharmacology, (2009) vol. 49, No. 9, pp. 1093.

Lipworth, Brian J. "Clinical pharmacology of b3-adrenoceptors" Br J Clin Pharmacol (1996) pp. 291-300.

McHale, Mary "Grignard Reaction" Connexions module: m15245, (2007) pp. 1-18.

McLaughlin, Mark., et al; Suzuki-Miyaura Cross-Coupling of Benzylic Phospahates with Arylboronic Acids; Organic Letters (2005) vol. 7 No. 22 pp. 4875-4878.

Meng, Wei et al "Discovery of Dapagliflozin: A Potent, Selective Renal Sodium-Dependent Glucose Cotransporter 2 (SGLT2) Inhibitor for the Treatment of Type 2 Diabetes" J. Med. Chem. (2008) vol. 51, pp. 1145-1149.

Merck Manual Online Edition, "Diabetes Mellitus" http://www.merckmanuals.com/professional/endocrine_and_metabolic_disorders/diabetes_mellitus_and_disorders of carbohyrate_metabolism/diabetes_mellitus_dm.html#v987998. last revision Jun. 2008 by Preeti Kishore M.D.

Mooradian, Arshang D. et al. "Narrative Review: A Rational Approach to Starting Insulin Therapy" (2006) Annals of Internal Medicine, vol. 145, pp. 125-134.

Neamati, Ouri., et al;, "Depsides and Depsidones as Inhibiton of HIV-1 Integrase: Dimvery of Novel Inhibitors Through 3D Database Searclung", J. Med. Chem., 1997, vol. 40, pp. 942-951.

Nobre, Sabrina M., et al; Synthesis of Diarylmethane Derivatives from Pd-Catalyzed Cross-Coupling Reactions of Benzylic Halides with Arylboronic Acids; Tetrahedron Letters (2004) vol. 45 8225-8228.

Oku, Akira., et al; T-1095, An Inhibitor or renal Na+-Glucose Cotransporters, May Provide a Novel Approach to Treating Diabetes; Diabetes (1999) vol. 48 pp. 1794-1800.

Perner, Richard J.; 5,6,7-Trisubstituted 4-Aminopyrido[2,3-d]pyrimidines as Novel inhibitors of Adenosime Kinase; Journal of Medicinal Chemistry (2003) vol. 46 pp. 5249-5257.

Piya, Milan K. et al. "Emerging treatment options for type 2 diabetes" British Journal of Clinical Pharmacology, (2010) vol. 70, No. 5, pp. 631-644.

Printz, Richard L. et al. "Tweaking the Glucose Sensor: Adjusting Glucokinase Activity with Activator Compounds" Endocrinology, (2005) vol. 146, No. 9, pp. 3693-3695.

Rainier, Jon D. et al. "Aluminum- and Boron-Mediated C-Glycoside Synthesis from 1,2-Anhydroglycosides" Organic Letters, (2000) vol. 2, No. 17, pp. 2707-2709.

Randzio, Stanislaw L. et al. "Metastability and Instability of Organic Crystalline Substances" J. Phys. Chem. (2008) 112, pp. 1435-1444.

Redenti, Enrico et al. "Drug/Cyclodextrin/Hydroxy Acid Multicomponent Systems. Properties and Pharmaceutical Applications" Journal of Pharmaceutical Sciences, (2000) vol. 89, No. 1, pp. 1-8.

Revesz, Lasslo., et al; SAR of Benzoylpylpyridines and Benzophenones as p38 Alpha MAP Kinase Inhibitors with Oral Activity; Bioorganic & Medicinal Chemistry Letters (2004) vol. 14 pp. 3601-3605.

Rudnic, Edward et al. "Oral Solid Dosage Forms" Remington's Pharmaceutical Sciences, 18th Ed, Gennaro, A.R. Ed, Macie Pub. Co. (1990) pp. 1633-1665.

Sherwin, Robert S. et al. "The Prevention or Delay of Type 2 Diabetes" Diabetes Care, (2002) vol. 25, No. 4, pp. 742-749.

Castelhano, Arlindo L. et al. "Reactions of an Electrophilic Glycine Cation Equivalent With Grignard Reagents a Simple Synthesis of β,g-Unsaturated Amino Acids" (1986) Tetrahedron Letters, vol. 27, No. 22, pp. 2435-2438.

Goodwin, Nicole C. et al. "Novel L-Xylose Derivatives as Selective Sodium-Dependent Glucose Cotransporter 2 (SGLT2) Inhibitors for the Treatment of Type 2 Diabetes" (2009) Journal Medicinal Chemistry vol. 52 pp. 6201-6204.

Silverman, et al. "Handbook of Grignard Reagents" Marcel Dekker (1996) p. 82.

Singhal, Dharmendra et al. "Drug polymorphism and dosage form design: a practical perspective" Advanced Drug Delivery Reviews, 56, (2004) pp. 335-347.

Sommer, Michael Bech., et al; Displacement of Halogen of 2-Halogeno-Substituted Benzonitriles with Carbonions. Preparation of (2-Cyanoaryl)arylacetonitriles; Journal of Organic Chemistry (1990) vol. 55 pp. 4817-4821.

Stazi, Federica., et al; Statistical Experimental Design-Driven Discovery of room-Temperature Conditions for Palladium-Catalyzed Cyanation of Aryl Bromides; Tetrahedron Letters (2005) vol. 46 1815-1818; Elsevier Ltd.

Tanaka, Chikako "Therapeutic Drugs for Metabolic Diseases, Chapter 2" (2002) New Yakurigaku (New Pharmacology) pp. 524-527.

Thomas, Leo et al. "(R)-8-(3-Amino-piperidin-l-yl)-7-but-2-ynyl-3-methyl-1-(4-methyl-quinazolin-2-ylmethyl)-3,7-dihydro-purine-2,6-dione (BI 1356), a Novel Xanthine-Based Dipeptidyl Peptidase 4 Inhibitor, Has a Superior Potency and Longer Duration of Action Compared with Other Dipeptidyl Peptidase-4 Inhibitors" Journal of Pharmacology and Experimental Therapeutics (2008) 325, pp. 175-182.

Thomson, Scott C. et al. "Acute and chronic effects of SGLT2 blockade on glomerular and tubular function in the early diabetic rat" (2011) Am J Physiol Regul Integr Comp Physiol, V 302, pp. R75-R83.

Threlfall, Terry "Structural and Thermodynamic Explanations of Ostwald's Rule" Organic Process Research & Development (2003) vol. 7, pp. 1017-1027.

Tykwinski, Rik R; Evolution in the Palladium-Catalyzed Cross-Coupling of sp- and sp2-Hybridized Carbon Atoms; Angew Chemical International Edition (2003) vol. 42 pp. 1566-1568.

U.S. Appl. No. 13/637,413, filed Sep. 26, 2012. Inventor: Rolf Grempler.

U.S. Appl. No. 13/785,365, filed Mar. 5, 2013. Inventor: Masanori Ito.

U.S. Appl. No. 13/833,097, filed Mar. 15, 2013. Inventor: Eric Williams Mayoux.

Ueta, Kiichiro., et al; Long-Term Treatment with the Na+-Glucose Cotransporter Inhibitor T-1095 Causes Sustained Improvement in Hyperglycemia and Prevents Diabetic Neuropathy in Goto-Kakizaki Rats; Life Sciences (2005) vol. 76 pp. 2655-2668.

Vallon, Volker et al. "Glomerular Hyperfiltration in Experimental Diabetes Melliutes: Potential Role of Tubular Reabsorption" (1999) J. Am. Soc. Nephrol., V 10: pp. 2569-2576.

Wallace, Debra A., et al; Cyclopropylboronic Acid: Synthesis and Suzuki Cross-Coupling Reactions; Tetrahedron Letters (2002) vol. 43 pp. 6987-6990; Pergamon Press.

Wang Y et al: "BI-1356. Dipeptidyl-peptidase IV inhibitor, antidiabetic agent" Drugs of the Future, Prous Science, ES,vol. 33, No. 6, Jun. 1, 2008, pp. 473-477.

Websters Third New International Dictionary, Editor: Gove, definition of prevent; 1963, 2 pgs.

Xue, Song., et al; Zinc-mediated Synthesis of Alpha-C-Glycosided from 1,2-Anhydroglycosides; Synletters (2003) vol. 6 pp. 870-872.

Yamada, Yuichiro et al. "Clinic: Careful Progress in the Field and new Therapeutic Methods" Medical Online, (2007) vol. 220, No. 13, pp. 1219-1221.

Yao, Chun-Hsu et al. "Discovery of Novel N-b-D-Xylosylindole Derivatives as Sodium-Dependent Glucose Cotransporter 2 (SGLT2) Inhibitors for the Management of Hyperglycemia in Diabetes" (2011) J. Med. Chem. vol. 54, pp. 166-178.

Zhang, L. et al "Dapagliflozin treatment in patients with different stages of type 2 diabetes mellitus: effects on glycaemic control and body weight" Diabetes, Obesity and Metabolism (2010) vol. 12, No. 6, p. 510-515.

Thomas, Leo et al. "(R)-8-(3-Amino-piperidin-1-yl)-7-but-2-ynyl-3-methyl-1-(4-methyl-quinazolin-2-ylmethyl)-3,7-dihydro-purine-2,6-dione (BI 1356), a Novel Xanthine-Based Dipeptidyl Peptidase 4 Inhibitor, Has a Superior Potency and Longer Duration of Action Compared with Other Dipeptidyl Peptidase-4 Inhibitors" Journal of Pharmacology and Experimental Therapeutics (2008) 325, pp. 175-182.

* cited by examiner

Figure 1: X-ray powder diffraction pattern of the crystalline form (background corrected)
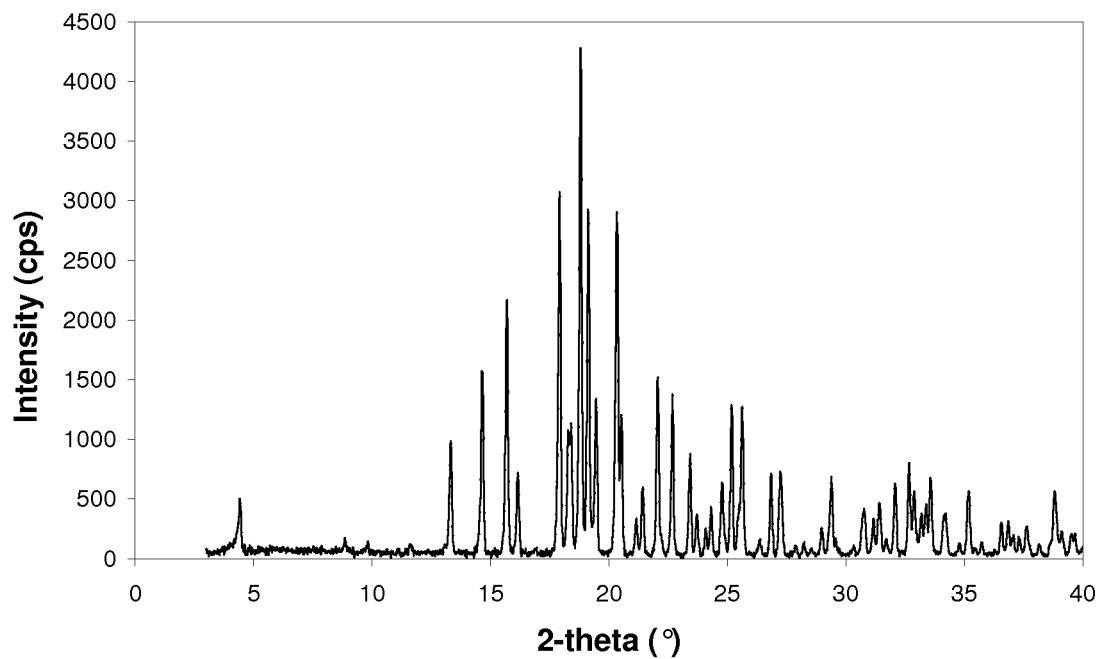
Figure 2: DSC diagram of the crystalline form
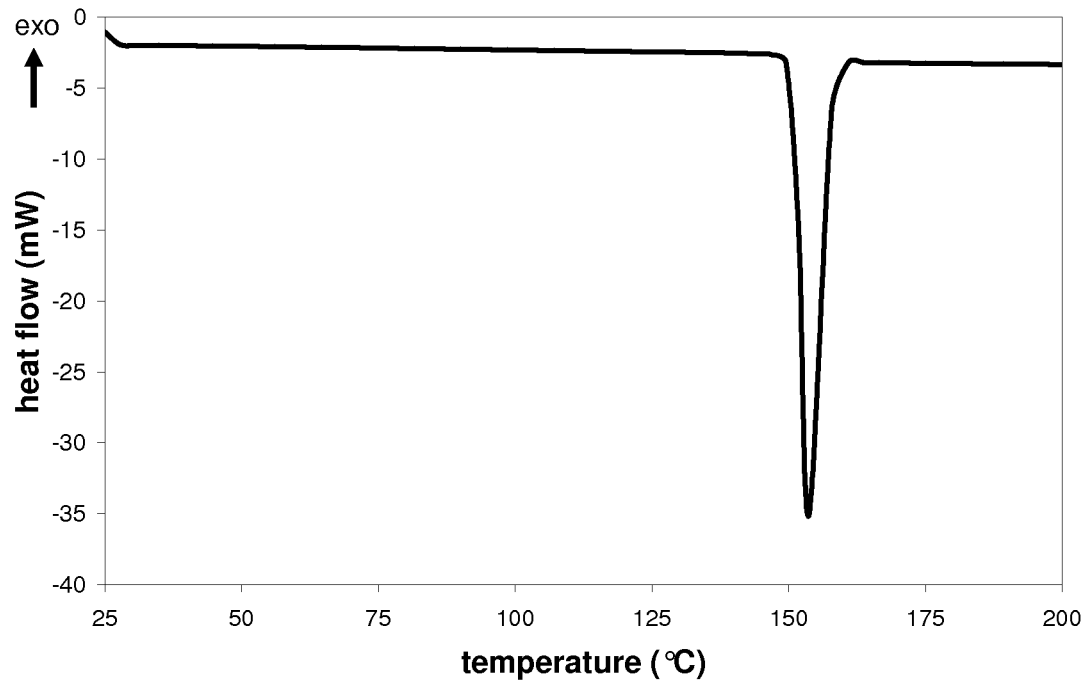

METHOD FOR THE PREPARATION OF A CRYSTALLINE FORM

The invention relates to a method for the preparation for a crystalline form of 1-chloro-4-(β-D-glucopyranos-1-yl)-2-[4-((S)-tetrahydrofuran-3-yloxy)-benzyl]-benzene. In addition the invention relates to a crystalline form obtainable by such a method and the use of the crystalline form for preparing medicaments.

BACKGROUND OF THE INVENTION

The compound 1-chloro-4-(β-D-glucopyranos-1-yl)-2-[4-((S)-tetrahydrofuran-3-yloxy)-benzyl]-benzene (in the following referred to it as "compound A") is described in the international patent application WO 2005/092877 and has the chemical structure according to formula A

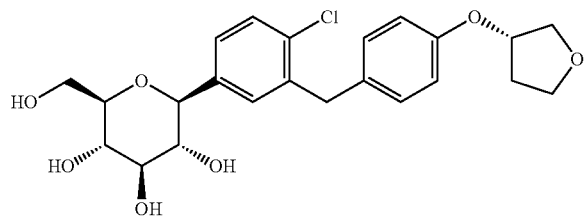

The compounds described therein have a valuable inhibitory effect on the sodium-dependent glucose cotransporter SGLT, particularly SGLT2.

The international patent application WO 2006/120208 describes various methods of synthesis of SGLT2 inhibitors, inter alia of the compound A.

A crystalline form of the compound A and a method for its preparation are described in the international application WO 2006/117359. As preferred solvents for example methanol, ethanol, isopropanol, ethyl acetate, diethylether, acetone, water and mixtures thereof are described for the crystallization process.

In the synthesis of the compound A, for example according to WO 2006/120208, it is observed that certain impurities may be found in the final substance. Furthermore it is found that crystallization processes as described in the WO 2006/117359 decrease the content of impurities and increase the purity of the compound, but not in a totally satisfactory manner.

It is well known to the one skilled in the art that in the pharmaceutical field highly pure compounds are desired. A very high purity may improve the stability in long-term storage. On the other hand impurities may be attributed to unwanted physico-chemical properties, for example hygroscopicity, or pharmacological side effects.

AIM OF THE INVENTION

The aim of the present invention is to find an advantageous method for preparing a crystalline form of a compound 1-chloro-4-(β-D-glucopyranos-1-yl)-2-[4-((S)-tetrahydrofuran-3-yloxy)-benzyl]-benzene; in particular a robust method with which the crystalline form may be obtained in a high purity, with a low content of certain impurities, and/or which allows the manufacture of the crystalline form in a commercial scale with a low technical expenditure and a high space/time yield.

Another aim of the present invention is to provide a crystalline form of 1-chloro-4-(β-D-glucopyranos-1-yl)-2-[4-((S)-tetrahydrofuran-3-yloxy)-benzyl]-benzene, in particular in a high purity.

A further aim of the present invention is to provide a pharmaceutical composition comprising the crystalline form.

Another aim of the present invention is to provide a use of the crystalline form.

Other aims of the present invention will become apparent to the skilled artisan directly from the foregoing and following description.

OBJECT OF THE INVENTION

In a first aspect the present invention relates to a method for preparing a crystalline form of a compound 1-chloro-4-(β-D-glucopyranos-1-yl)-2-[4-((S)-tetrahydrofuran-3-yloxy)-benzyl]-benzene comprising the following steps:

(a) dissolving the compound in a mixture of at least two solvents to form a solution wherein the first solvent is selected from the group of solvents consisting of toluene and tetrahydrofuran, and the second solvent is selected from the group of solvents consisting of methanol, ethanol, 1-propanol and 2-propanol, or the first solvent is ethanol and the second solvent is selected from the group of solvents consisting of ethylacetate, n-propylacetate and methylethylketone;

(b) storing the solution to precipitate the crystalline form of the compound out of solution;

(c) isolating the crystalline form of the compound from the solution.

It is found that with the method according to this invention the crystalline form can be obtained in a high purity and in a high yield, in particular at commercially viable scales. The method shows a low technical expenditure and a high space/time yield. Despite possible variations in the purity of the starting material the method yields the crystalline form in a high purity. In particular the following impurities of the formulas IMP.1 and IMP.2 can be depleted to a high degree:

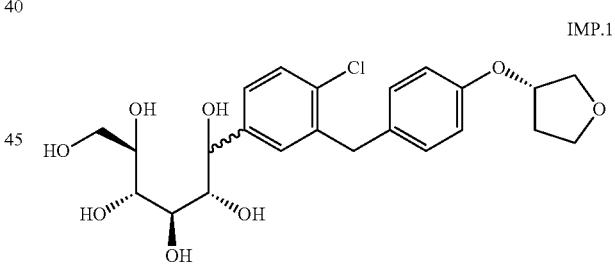

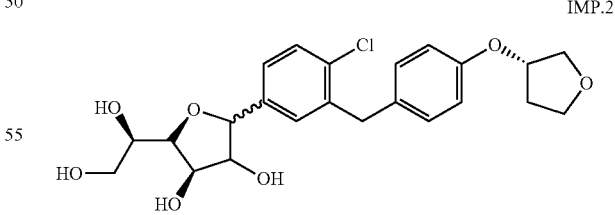

In another aspect the present invention relates to the crystalline form of a compound 1-chloro-4-(β-D-glucopyranos-1-yl)-2-[4-((S)-tetrahydrofuran-3-yloxy)-benzyl]-benzene obtainable by a process as described hereinbefore and hereinafter.

In another aspect the present invention relates to the crystalline form of a compound 1-chloro-4-(β-D-glucopyranos-1-yl)-2-[4-((S)-tetrahydrofuran-3-yloxy)-benzyl]-benzene having an X-ray powder diffraction pattern that comprises peaks at 18.84, 20.36 and 25.21 degrees 2Θ (±0.1 degrees 2Θ), wherein said X-ray powder diffraction pattern is made using CuK$_{\alpha1}$ radiation, characterized by a purity above 99% as measured by HPLC.

In yet another aspect the present invention relates to a pharmaceutical composition comprising the crystalline form as described hereinbefore and hereinafter.

In yet another aspect the present invention relates to a use of the crystalline form as described hereinbefore and hereinafter for preparing a pharmaceutical composition which is suitable for the treatment or prevention of metabolic disorders, in particular of a metabolic disorder selected from the group consisting of type 1 and type 2 diabetes mellitus, complications of diabetes, metabolic acidosis or ketosis, reactive hypoglycaemia, hyperinsulinaemia, glucose metabolic disorder, insulin resistance, metabolic syndrome, dyslipidaemias of different origins, atherosclerosis and related diseases, obesity, high blood pressure, chronic heart failure, oedema and hyperuricaemia.

Further aspects of the present invention become apparent to the one skilled in the art from the following detailed description of the invention and the examples.

BRIEF DESCRIPTION OF THE FIGURES

The FIG. 1 shows a background corrected X-ray powder diffractogram of the crystalline form of the compound A.

The FIG. 2 shows the thermoanalysis via DSC of the crystalline form of the compound A.

DETAILED DESCRIPTION OF THE INVENTION

This crystalline form of the compound A may be identified by means of their characteristic X-ray powder diffraction (XRPD) patterns, in particular as described in the WO 2006/117359.

The crystalline form is characterised by an X-ray powder diffraction pattern that comprises peaks at 18.84, 20.36 and 25.21 degrees 2Θ (±0.1 degrees 2Θ), wherein said X-ray powder diffraction pattern is made using CuK$_{\alpha1}$ radiation.

In particular said X-ray powder diffraction pattern comprises peaks at 14.69, 18.84, 19.16, 19.50, 20.36 and 25.21 degrees 2Θ (±0.1 degrees 2Θ), wherein said X-ray powder diffraction pattern is made using CuK$_{\alpha1}$ radiation.

Said X-ray powder diffraction pattern is even more characterised by peaks at 14.69, 17.95, 18.84, 19.16, 19.50, 20.36, 22.71, 23.44, 24.81 and 25.21 degrees 2Θ (±0.1 degrees 2Θ), wherein said X-ray powder diffraction pattern is made using CuK$_{\alpha1}$ radiation.

More specifically, the crystalline form of the compound A is characterised by an X-ray powder diffraction pattern, made using CuK$_{\alpha1}$ radiation, which comprises peaks at degrees 2Θ (±0.1 degrees 2Θ) as contained in the Table 1 of WO 2006/117359 or as contained in the Table 1 of the Experiment A of the present application or as shown in the FIG. 1 of WO 2006/117359 or as shown in the FIG. 1 of the present application.

Furthermore the crystalline form of the compound A is characterised by a melting point of about 151° C.±5° C. (determined via DSC; evaluated as onset-temperature; heating rate 10 K/min).

The X-ray powder diffraction patterns are recorded, within the scope of the present invention, using a STOE-STADI P-diffractometer in transmission mode fitted with a location-sensitive detector (OED) and a Cu-anode as X-ray source (CuKα1 radiation, λ=1.54056 Å, 40 kV, 40 mA).

In order to allow for experimental error, the above described 2Θ values should be considered accurate to ±0.1 degrees 2Θ, in particular ±0.05 degrees 2Θ. That is to say, when assessing whether a given sample of crystals of the compound A is the crystalline form in accordance with the invention, a 2 Θ value which is experimentally observed for the sample should be considered identical with a characteristic value described above if it falls within ±0.1 degrees 2Θ, in particular ±0.05 degrees 2Θ of the characteristic value.

The melting point is determined by DSC (Differential Scanning calorimetry) using a DSC 821 (Mettler Toledo).

The present invention relates to a method for preparing a crystalline form of the compound A comprising the following steps:

(a) dissolving the compound A in a mixture of at least two solvents to form a solution wherein the first solvent is selected from the group of solvents consisting of toluene and tetrahydrofuran, and the second solvent is selected from the group of solvents consisting of methanol, ethanol, 1-propanol and 2-propanol, or the first solvent is ethanol and the second solvent is selected from the group of solvents consisting of ethylacetate, n-propylacetate and methylethylketone;

(b) storing the solution to precipitate the crystalline form of the compound A out of solution;

(c) isolating the crystalline form of the compound A from the solution.

The first solvent is preferably selected from the group of solvents consisting of toluene and tetrahydrofuran.

The second solvent is preferably selected from the group of solvents consisting of methanol, ethanol, 1-propanol and 2-propanol; even more preferably from the group of solvents consisting of ethanol, 1-propanol and 2-propanol.

According to a preferred alternative the first solvent is ethanol and the second solvent is n-propylacetate or ethylacetate.

Examples of mixtures of at least two solvents are toluene/methanol, toluene/ethanol, toluene/1-propanol, toluene/2-propanol, tetrahydrofuran/methanol, tetrahydrofuran/ethanol, tetrahydrofuran/1-propanol, tetrahydrofuran/2-propanol, ethanol/n-propylacetate, ethanol/ethylacetate, ethanol/methylethylketone.

Preferred examples of mixtures of at least two solvents are toluene/ethanol, toluene/1-propanol, toluene/2-propanol, tetrahydrofuran/ethanol, tetrahydrofuran/1-propanol, tetrahydrofuran/2-propanol, ethanol/n-propylacetate, ethanol/ethylacetate.

The weight ratio of the first solvent to the second solvent is preferably in the range from about 1:10 to 10:1, more preferably from about 1:5 to 5:1, even more preferably from about 1:2 to 2:1, most preferably about 1:1.

With regard to the preferred examples toluene/ethanol, toluene/1-propanol, toluene/2-propanol, ethanol/n-propylacetate, ethanol/ethylacetate the weight ratio of the first solvent to the second solvent is preferably in the range from about 1:5 to 5:1, more preferably from about 1:2 to 2:1, most preferably about 1:1.

With regard to the preferred examples tetrahydrofuran/ethanol, tetrahydrofuran/1-propanol, tetrahydrofuran/2-propanol, the weight ratio of the first solvent to the second solvent is preferably in the range from about 1:10 to 2:1, more preferably from about 1:5 to 1:1, even more preferably from about 1:4 to 1:2.

In the step (a) the compound A may be employed in an amorphous or crystalline form or as a solution, for example obtained in the synthesis of the compound A.

Preferably the solution obtained in the step (a) is a saturated or nearly saturated solution at the given temperature.

The terms "saturated" or "nearly saturated" are related to the starting material of the compound A as used in step (a). For example a solution which is saturated with respect to the starting material of the compound A may be supersaturated with respect to its crystalline form.

The weight ratio of the compound A relative to the mixture of solvents is preferably in the range 1:8 to 1:2, more preferably 1:6 to 1:3, even more preferably from 1:5 to 1:4.

In the step (a) the solution may be heated up to the boiling temperature of the solution or to a temperature in the range from about 60° C. to 120° C., for example about 100° C. The solution obtained in the step (a) may be filtered, for example over charcoal.

At the beginning of the step (b) seeding crystals of the compound A are preferably added to the solution obtained in the step (a), optionally after a filtration step. The amount of the seeding crystals relative to the total amount of the compound A may be in the range from up to about 5 weight-%, more preferably from about 0.001 to 1 weight-%. The seeding crystals may be obtained for example by a process as described in the WO 2006/117359. The seeding crystals are preferably added at a temperature in the range from about 30° C. to 80° C., most preferably about 60 to 75° C. Alternatively the crystallization may be induced by methods as known in the art, for example by scratching or rubbing.

In the step (b) the temperature is preferably lowered in order to obtain a high yield of the precipitated crystalline form of the compound A. The temperature may be lowered continuously or via a predefined cooling ramp. An example of a cooling ramp is within about 30 min to 60±5° C., then within about 90 min to 50±5° C., then within about 60 min to 40±5° C., then within about 60 min to 25±5° C. A preferred final temperature at the end of the step (b) is in the range from about −10° C. to 40° C., more preferably from about 0° C. to 35° C., most preferably from about 10° C. to 30° C.

The duration of the step (b) may be in the range from about 30 min to 48 hours, preferably from about 3 to 6 hours.

The step (b) can be carried out with or without stirring. As known to the one skilled in the art by the period of time and the difference of temperature in step (b) the size, shape and quality of the obtained crystals can be varied.

In the step (c) the obtained crystals are isolated, for example via centrifugation or filtration. The obtained crystals are preferably washed with a solvent or a mixture of solvents, wherein the solvent is preferably selected from the group consisting of methanol, ethanol, 1-propanol, 2-propanol or tert.-butylmethylether. The most preferred solvent is ethanol. Preferably remaining solvent(s) are advantageously removed from the crystals in a drying step, preferably at a temperature in the range from about 0° C. to 100° C., for example from about 50° C. to 80° C. The temperature, the pressure and the duration of this drying step may be chosen in order to lower the content of one or more solvents below a given value. For example the content of toluene in the crystalline form may be chosen to be equal or below 890 ppm, preferably below 500 ppm, even more preferably below 300 ppm. The content of ethanol in the crystalline form may be chosen to be equal or below 5000 ppm, preferably below 2000 ppm, even more preferably below 1000 ppm.

The compound A may be synthesized by methods as specifically and/or generally described or cited in the international application WO 2005/092877. Furthermore the biological properties of the compound A may be investigated as it is described in the international application WO 2005/092877 which in its entirety is incorporated herein by reference.

The crystalline form in accordance with the invention is preferably employed as drug active substance in substantially pure form, that is to say, essentially free of other crystalline forms of the compound A. Nevertheless, the invention also embraces the crystalline form as herein defined in admixture with another crystalline form or forms. Should the drug active substance be a mixture of crystalline forms, it is preferred that the substance comprises at least 50% of the crystalline form as described herein.

According to another aspect of the present invention the crystalline form of the compound A having an X-ray powder diffraction pattern that comprises peaks at 18.84, 20.36 and 25.21 degrees 2Θ (±0.1 degrees 2Θ), wherein said X-ray powder diffraction pattern is made using $CuK_{\alpha1}$ radiation is characterized by a purity above 99% as measured by HPLC. Preferably the purity is above 99.5%, even more preferably above 99.7%, most preferably above 99.8%.

In a preferred embodiment the crystalline form as defined hereinbefore is characterized by a content of the compound of the formula IMP.1

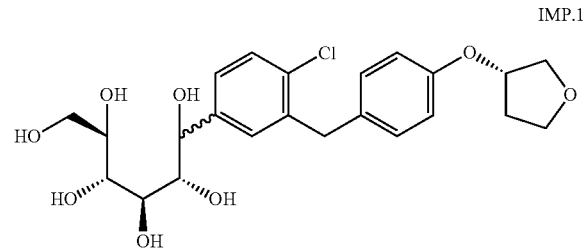 [SMILES: OC[C@H](O)[C@@H](O)[C@H](O)[C@@H](O)C(O)c1ccc(Cl)c(Cc2ccc(O[C@H]3CCOC3)cc2)c1]

IMP.1 equal or below 1.00% as measured by HPLC. Preferably the content of the compound of the formula IMP.1 is equal or below 0.15%, even more preferably equal or below 0.05% as measured by HPLC.

In another preferred embodiment the crystalline form as defined hereinbefore is characterized by a content of the compound of the formula IMP.2

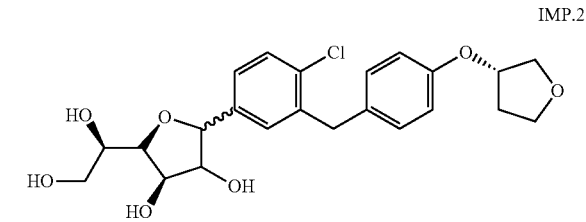

IMP.2 equal or below 0.15% as measured by HPLC. Preferably the content of the compound of the formula IMP.2 is equal or below 0.05% as measured by HPLC.

According to a more preferred embodiment the crystalline form is characterized by a content of the compounds of the formulas IMP.1 and IMP.2 as defined above.

The hereinbefore and hereinafter mentioned purity and impurity may be determined with methods known to the one skilled in the art. Preferably the purity and impurity is measured via HPLC. The purity is preferably determined as 100% minus the sum of all quantified impurities.

Preferably the HPLC device is equipped with a C18 column, in particular a column with a microparticulate C18 packing used for reversed-phase HPLC, for example prepared by chemically bonding a sterically-protected C18 stationary phase (e.g. diisobutyl n-octadecylsilane) to porous silica microspheres (e.g. with a pore size of about 80 Å). Advantageous dimensions of the column and microspheres are 4.6 mm (inner dimension)×50 mm column and 1.8 μm. A UV-detection is preferred, for example at 224 nm.

Typical parameters for such a HPLC are:
Device: HPLC with UV-detection
Column: C18, 1.8 μm, 50*4.6 mm
Column temperature: 20° C.
Gradient:

| time (min) | eluent A (%) | eluent B (%) |
|---|---|---|
| 0 | 100 | 0 |
| 1 | 70 | 30 |
| 4 | 70 | 30 |
| 8 | 5 | 95 |
| 12 | 5 | 95 |

Flow rate: 1.5 mL/min
Analysis time: 12 min
Equilibration time: 4 min
Injection volume: 8 μl
Detection: 224 nm
Preferred eluents are:
Eluent A: water+0.1% trifluoroacetic acid
Eluent B: acetonitrile+0.1% trifluoroacetic acid A preferred solvent for the samples or as blank solution is a 50/50 (v/v) mixture of acetonitrile/water. Preferably all solvents including water are HPLC grade.

In view of their ability to inhibit the SGLT activity, the crystalline form according to the invention is suitable for the preparation of pharmaceutical compositions for the treatment and/or preventative treatment of all those conditions or diseases which may be affected by the inhibition of the SGLT activity, particularly the SGLT-2 activity. Therefore, the crystalline form is particularly suitable for the preparation of pharmaceutical compositions for prevention or treatment of diseases, particularly metabolic disorders, or conditions such as type 1 and type 2 diabetes mellitus, complications of diabetes (such as e.g. retinopathy, nephropathy or neuropathies, diabetic foot, ulcers, macroangiopathies), metabolic acidosis or ketosis, reactive hypoglycaemia, hyperinsulinaemia, glucose metabolic disorder, insulin resistance, metabolic syndrome, dyslipidaemias of different origins, atherosclerosis and related diseases, obesity, high blood pressure, chronic heart failure, oedema and hyperuricaemia. The crystalline form is also suitable for the preparation of pharmaceutical compositions for preventing beta-cell degeneration such as e.g. apoptosis or necrosis of pancreatic beta cells. The crystalline form is also suitable for the preparation of pharmaceutical compositions for improving or restoring the functionality of pancreatic cells, and also of increasing the number and size of pancreatic beta cells. The crystalline form according to the invention may also be used for the preparation of pharmaceutical compositions useful as diuretics or antihypertensives and suitable for the prevention and treatment of acute renal failure.

By the administration of the crystalline form according to this invention an abnormal accumulation of fat in the liver may be reduced or inhibited. Therefore according to another aspect of the present invention there is provided a method for preventing, slowing, delaying or treating diseases or conditions attributed to an abnormal accumulation of liver fat in a patient in need thereof characterized in that a pharmaceutical composition according to the present invention is administered. Diseases or conditions which are attributed to an abnormal accumulation of liver fat are particularly selected from the group consisting of general fatty liver, non-alcoholic fatty liver (NAFL), non-alcoholic steatohepatitis (NASH), hyperalimentation-induced fatty liver, diabetic fatty liver, alcoholic-induced fatty liver or toxic fatty liver.

In particular, the crystalline form according to the invention is suitable for the preparation of pharmaceutical compositions for the prevention or treatment of diabetes, particularly type 1 and type 2 diabetes mellitus, and/or diabetic complications.

In addition the crystalline form according to the invention is particularly suitable for the prevention or treatment of overweight, obesity (including class I, class II and/or class III obesity), visceral obesity and/or abdominal obesity.

The dosage required to achieve the corresponding activity for treatment or prevention usually depends on the patient, the nature and gravity of the illness or condition and the method and frequency of administration and is for the patient's doctor to decide. Expediently, the dosage may be from 1 to 100 mg by oral route, in each case administered 1 to 4 times a day. For this purpose, the pharmaceutical compositions according to this invention preferably comprise the crystalline form together with one or more inert conventional carriers and/or diluents. Such pharmaceutical compositions may be formulated as conventional galenic preparations such as plain or coated tablets, capsules, powders, suspensions or suppositories.

The following example of synthesis serves to illustrate a method of preparing the compound A and its crystalline form. It is to be regarded only as a possible method described by way of example, without restricting the invention to its contents.

Determination of the Purity or Impurity Via HPLC:

This method is used for the determination of organic impurities in the compound A. The quantification is carried out via external standard solutions. The reagents (acetonitrile, water, trifluoroacetic acid (TFA)) are use in HPLC grade. The term "compound $A_{XX}$" denotes the crystalline form of the compound A as obtained with a method according to this invention.

Mobile Phase
Eluent A: water+0.1% TFA
Eluent B: acetonitrile+0.1% TFA
Solutions
Solvent: acetonitrile/water (50/50 (v/v))
Blank solution: solvent
Solution 1

A solution with a concentration of 0.5 mg/ml of the compound IMP.2 is prepared; e.g. 25 mg of the substance are weighed, dissolved in 2 mL of methanol and diluted with solvent to a total volume of 50 mL.

System Suitability Solution (SST)

A solution with a concentration of 0.5 mg/ml of the compound $A_{XX}$ is prepared, containing approx. 0.5% IMP.2; e.g. 25 mg of the compound $A_{XX}$ are weighed, dissolved in 2 mL of methanol (via ultrasound) and, after addition of 250 μL of solution 1, diluted with solvent to a total volume of 50 mL. Optional, approx. 0.5% of the following possible impurities may be added: IMP.1

Reporting Limit (0.05%)

A solution with 0.05% of the nominal concentration is prepared. Therefore, 50 μl of a stem solution is diluted with solvent to a total volume of 100 mL Sample Solutions A solution of the substance to be analyzed is prepared with a concentration of 0.8 mg/mL. Therefore, e.g. 40 mg of the substance are weighed, dissolved in 2 mL of methanol and diluted with solvent to a total volume of 50 mL. This solution is prepared twice.

Stem Solutions

A solution of the compound $A_{XX}$ is prepared with a concentration of 0.8 mg/mL. Therefore, e.g. 40 mg of the substance are weighed, dissolved with 2 mL of methanol and diluted with solvent to a total volume of 50 mL. This solution is prepared twice.

Reference Solution (0.5%)

A solution of compound $A_{XX}$ with a concentration of 4 µg/ml compared to the nominal weighed sample is prepared. Therefore, e.g. 250 µl of the stem solution are diluted with 50 mL. This solution is prepared twice (once from each stem solution).

Chromatographic Parameters:

Device: HPLC with UV-detection
Column: Zorbax SB-C18, 1.8 µm, 50*4.6 mm, (manufacturer: Agilent)
Column temperature: 20° C.
Gradient:

| Gradient: | | |
|---|---|---|
| time (min) | eluent A (%) | eluent B (%) |
| 0 | 100 | 0 |
| 1 | 70 | 30 |
| 4 | 70 | 30 |
| 8 | 5 | 95 |
| 12 | 5 | 95 |

Flow rate: 1.5 mL/min
Analysis time: 12 min
Equilibration time: 4 min
Injection volume: 8 µl
Detection: 224 nm
Injections:

| Injections: | |
|---|---|
| Solutions | Injections |
| Blank solution | n ≥ 1 |
| Reporting limit | 1 |
| Reference solution 1 | 2 |
| Reference solution 2 | 2 |
| SST | 1 |
| Blind solution | n ≥ 1 |

| Injections: | |
|---|---|
| Solutions | Injections |
| Sample 1, Solution 1 | 2 |
| Sample 1, Solution 2 | 2 |
| Sample 2, Solution 1 | 2 |
| Sample 2, Solution 2 | 2 |
| Further samples | 2 each |
| SST | 1 |

Typical Retention Times:

The order of elution of the peaks in the chromatogram of the SST-solution should correspond to a example chromatogram. The peak assignment is carried out with a example chromatogram or via the relative retention times (RRTs).

| Substance | RT (approx. min) | RRT |
|---|---|---|
| IMP.1 | 3.35 | 0.84 |
| Compound $A_{XX}$ | 3.97 | 1.00 |
| IMP.2 Isomer 1 | 4.97 | 1.25 |
| IMP.2 Isomer 2 | 5.19 | 1.31 |

Evaluation:

The calculation of the content of the impurities is carried out according to the following formula.

$$\% \text{ Impurity} = \frac{\overline{PF_{Sample}} * V_{Sample}}{EW_{Sample}} * \frac{\overline{EW_{Stem\ Solution}} * Potency_{Reference\ Substance}}{PF_{0.5\ Comparison} * V_{Stem\ Solution} * VF} * 100$$

$PF_X$: Peak areas
$EW_X$: weigh-in
Vx: volume to which the dilution is carried out
VF: dilution factor
Potency: known potency in % of the compound $A_{XX}$ reference substance The purity of a sample of the compound A is calculated as 100% minus the sum of all quantified impurities.

Preparation of the Compound A:

The terms "room temperature" or "ambient temperature" denote a temperature of about 20° C.

GC gas chromatography
hrs hours
i-Pr iso-propyl
Me methyl
min minute(s)
THF tetrahydrofuran

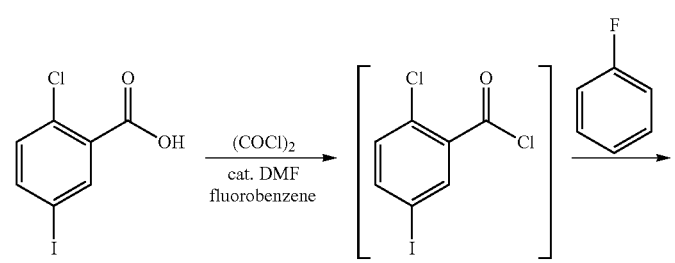

IX.1

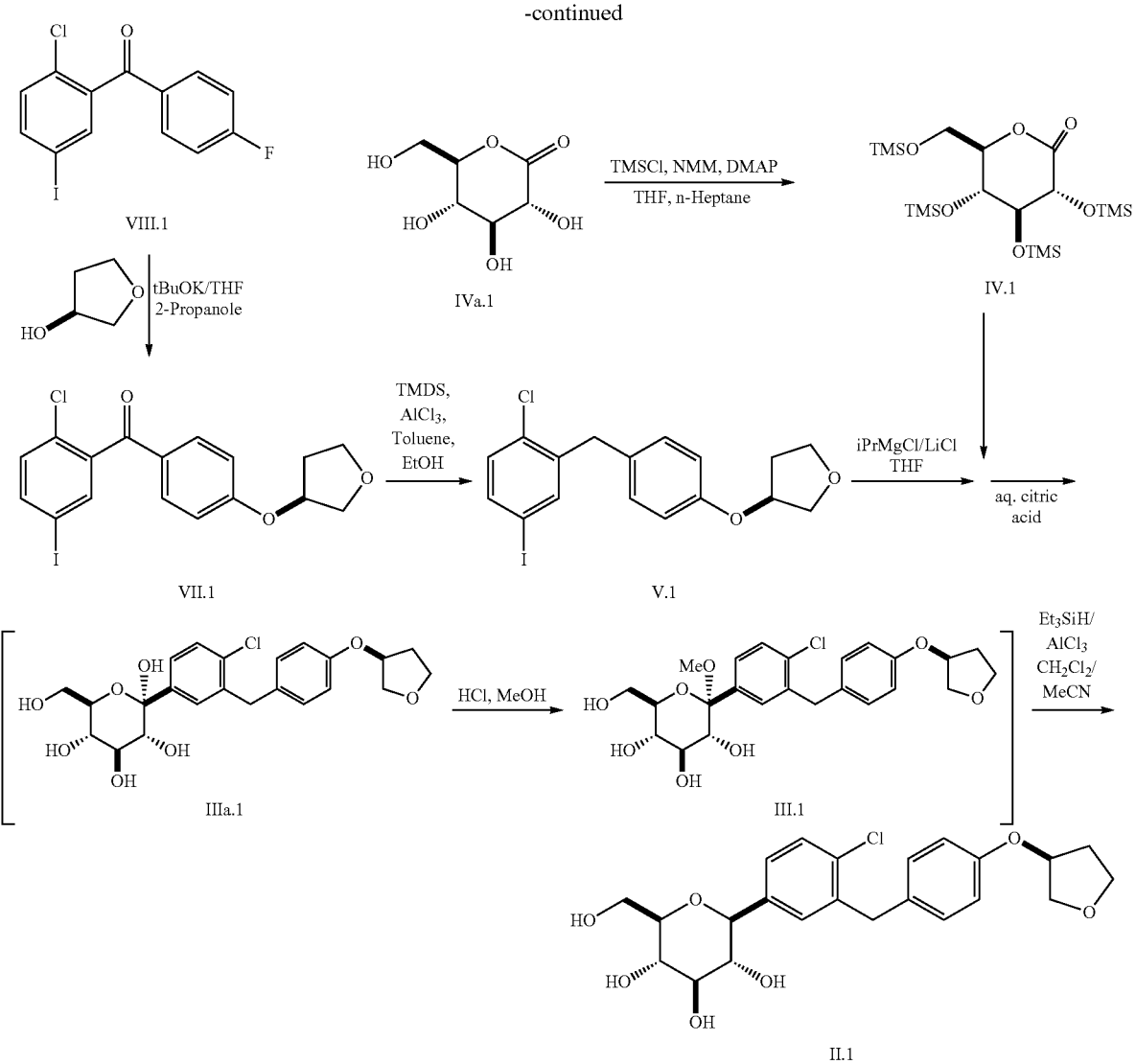

Example 1

Synthesis of the Fluoride VIII.1

Oxalylchloride (176 kg; 1386 mol; 1.14 eq) is added to a mixture of 2-chloro-5-iodo benzoic acid (343 kg; 1214 mol) (compound IX.1), fluorobenzene (858 kg) and N,N-dimethylformamide (2 kg) within 3 hours at a temperature in the range from about 25 to 30° C. (gas formation). After completion of the addition, the reaction mixture is stirred for additional 2 hours at a temperature of about 25 to 30° C. The solvent (291 kg) is distilled off at a temperature between 40 and 45° C. (p=200 mbar). Then the reaction solution (911 kg) is added to aluminiumchloride AlCl$_3$ (181 kg) and fluorobenzene (192 kg) at a temperature between about 25 and 30° C. within 2 hours. The reaction solution is stirred at the same temperature for about an additional hour. Then the reaction mixture is added to an amount of 570 kg of water within about 2 hours at a temperature between about 20 and 30° C. and stirred for an additional hour. After phase separation the organic phase (1200 kg) is separated into two halves (600 kg each). From the first half of the organic phase solvent (172 kg) is distilled off at a temperature of about 40 to 50° C. (p=200 mbar). Then 2-propanole (640 kg) is added. The solution is heated to about 50° C. and then filtered through a charcoal cartouche (clear filtration). The cartouche may be exchanged during filtration and washed with a fluorobenzene/2-propanole mixture (1:4; 40 kg) after filtration. Solvent (721 kg) is distilled off at a temperature of about 40 to 50° C. and p=200 mbar. Then 2-propanole (240 kg) is added at a temperature in the range between about 40 to 50° C. If the content of fluorobenzene is greater than 1% as determined via GC, another 140 kg of solvent are distilled off and 2-propanole (140 kg) is added. Then the solution is cooled from about 50° C. to 40° C. within one hour and seeding crystals (50 g) are added. The solution is further cooled from about 40° C. to 20° C. within 2 hours. Water (450 kg) is added at about 20° C. within 1 hour and the suspension is stirred at about 20° C. for an additional hour before the suspension is filtered. The filter cake is washed with 2-propanole/water (1:1; 800 kg). The product is dried until a water level of <0.06% w/w is obtained. The second half of the organic phase is processed identically. A total of 410 kg (94% yield) of product which has a white to off-white crystalline appearance, is obtained. The identity of the product is determined via infrared spectrometry.

Example 2

Synthesis of the Ketone VII.1

To a solution of the fluoride VIII.1 (208 kg), tetrahydrofuran (407 kg) and (S)-3-hydroxytetrahydrofuran (56 kg) is added potassium-tert-butanolate solution (20%) in tetrahydrofuran (388 kg) within 3 hrs at 16 to 25° C. temperature. After completion of the addition, the mixture is stirred for 60 min at 20° C. temperature. Then the conversion is determined via HPLC analysis. Water (355 kg) is added within 20 min at a temperature of 21° C. (aqueous quench). The reaction mixture is stirred for 30 min (temperature: 20° C.). The stirrer is switched off and the mixture is left stand for 60 min (temperature: 20° C.). The phases are separated and solvent is distilled off from the organic phase at 19 to 45° C. temperature under reduced pressure. 2-Propanol (703 kg) is added to the residue at 40 to 46° C. temperature and solvent is distilled off at 41 to 50° C. temperature under reduced pressure. 2-Propanol (162 kg) is added to the residue at 47° C. temperature and solvent is distilled off at 40 to 47° C. temperature under reduced pressure. Then the mixture is cooled to 0° C. within 1 hr 55 min. The product is collected on a centrifuge, washed with a mixture of 2-propanol (158 kg) and subsequently with tert.-butylmethylether (88 kg) and dried at 19 to 43° C. under reduced pressure. 227 kg (91.8%) of product are obtained as colourless solid. The identity of the product is determined via infrared spectrometry.

Example 3

Synthesis of the Iodide V.1

To a solution of ketone VII.1 (217.4 kg) and aluminium chloride (AlCl$_3$; 81.5 kg) in toluene (366.8 kg) is added 1,1,3,3-tetramethyldisiloxane (TMDS, 82.5 kg) within 1 hr 30 min (temperature: 18-26° C.). After completion of the addition, the mixture is stirred for additional 1 hr at a temperature of 24° C. Then the conversion is determined via HPLC analysis. Subsequently the reaction mixture is treated with acetone (15.0 kg), stirred for 1 hr 5 min at 27° C. temperature and the residual TMDS content is analyzed via GC. Then a mixture of water (573 kg) and concentrated HCl (34 kg) is added to the reaction mixture at a temperature of 20 to 51° C. (aqueous quench). The reaction mixture is stirred for 30 min (temperature: 51° C.). The stirrer is switched off and the mixture is left stand for 20 min (temperature: 52° C.). The phases are separated and solvent is distilled off from the organic phase at 53-73° C. temperature under reduced pressure. Toluene (52.8 kg) and ethanol (435.7 kg) are added to the residue at 61 to 70° C. temperature. The reaction mixture is cooled to 36° C. temperature and seeding crystals (0.25 kg) are added. Stirring is continued at this temperature for 35 min. Then the mixture is cooled to 0 to 5° C. and stirred for additional 30 min. The product is collected on a centrifuge, washed with ethanol (157 kg) and dried at 15 to 37° C. under reduced pressure. 181 kg (82.6%) of product are obtained as colourless solid. The identity of the product is determined via the HPLC retention time.

Example 4

Synthesis of the Lactone IV.1

A suspension of the D-(+)-gluconic acid-delta-lactone IVa.1 (42.0 kg), tetrahydrofuran (277.2 kg), 4-methylmorpholine (NMM; 152.4 kg) and 4-dimethylaminopyridine (DMAP; 1.44 kg) is treated with chlorotrimethylsilane (TMSCl; 130.8 kg) within 50 min at 13 to 19° C. After completion of the addition stirring is continued for 1 hr 30 min at 20 to 22° C. and the conversion is determined via HPLC analysis. Then n-heptane (216.4 kg) is added and the mixture is cooled to 5° C. Water (143 kg) is added at 3 to 5° C. within 15 min. After completion of the addition the mixture is heated to 15° C. and stirred for 15 min. The stirrer is switched off and the mixture is left stand for 15 min. Then the phases are separated and the organic layer is washed in succession two times with water (143 kg each). Then solvent is distilled off at 38° C. under reduced pressure and n-heptane (130 kg) is added to the residue. The resulting solution is filtered and the filter is rinsed with n-heptane (63 kg) (filter solution and product solution are combined). Then solvent is distilled off at 39 to 40° C. under reduced pressure. The water content of the residue is determined via Karl-Fischer analysis (result: 0.0%). 112.4 kg of the product is obtained as an oil (containing residual n-heptane, which explains the yield of >100%). The identity of the product is determined via infrared spectrometry.

Example 5a

Synthesis of the Glucoside II.1

To a solution of the iodide V.1 (267 kg) in tetrahydrofuran (429 kg) is added Turbogrignard solution (isopropylmagnesium chloride/lithium chloride solution, 14 weight-% iPrMgCl in THF, molar ratio LiCl:iPrMgCl=0.9-1.1 mol/mol) (472 kg) at −21 to −15° C. temperature within 1 hr 50 min. On completion of the addition the conversion is determined via HPLC analysis. The reaction is regarded as completed when the area of the peak corresponding to the iodide V.1 is smaller than 5.0% of the total area of both peaks, iodide V.1 and the corresponding desiodo compound of iodide V.1. If the reaction is not completed, additional Turbogrignard solution is added until the criterion is met. In this particular case the result is 3.45%. Then the lactone IV.1 (320 kg) is added at −25 to −18° C. temperature within 1 hr 25 min. The resulting mixture is stirred for further 1 hr 30 min at −13 to −18° C. On completion of the addition the conversion is determined via HPLC analysis (for information). On completion, a solution of citric acid in water (938 L; concentration: 10%-weight) is added to the reaction mixture of a volume of about 2500 L at −13 to 19° C. within 1 hr 25 min. The solvent is partially distilled off from the reaction mixture (residual volume: 1816-1905 L) at 20 to 30° C. under reduced pressure and 2-methyltetrahydrofuran (532 kg) is added. Then the stirrer is switched off and the phases are separated at 29° C. After phase separation the pH value of the organic phase is measured with a pH electrode (Mettler Toledo MT HA 405 DPA SC) or alternatively with pH indicator paper (such as pH-Fix 0-14, Macherey and Nagel). The measured pH value is 2 to 3. Then solvent is distilled off from the organic phase at 30 to 33° C. under reduced pressure and methanol (1202 kg) is added followed by the addition of a solution of 1.25N HCl in methanol (75 kg) at 20° C. (pH=0). Full conversion to the acetale III.1 is achieved by subsequent distillation at 20 to 32° C. under reduced pressure and addition of methanol (409 kg).

Completion of the reaction is obtained when two criteria are fulfilled:

1) The ratio of the sum of the HPLC-area of the alpha-form+beta-form of intermediate III.1 relative to the area of intermediate IIIa.1 is greater or equal to 96.0%:4.0%.

2) The ratio of the HPLC-area of the alpha-form of intermediate III.1 to the beta-form of III.1 is greater or equal to 97.0% to 3.0%.

In this particular case both criteria are met. Triethylamin (14 kg) is added (pH=7.4) and solvent is distilled off under reduced pressure, acetonitrile (835 kg) is added and further distilled under reduced pressure. This procedure is repeated (addition of acetonitrile: 694 kg) and methylene chloride (640 kg) is added to the resulting mixture to yield a mixture of the acetale III.1 in acetonitrile and methylene chloride. The water content of the mixture is determined via Karl Fischer titration (result: 0.27%).

The reaction mixture is then added within 1 hr 40 min at 10 to 19° C. to a preformed mixture of $AlCl_3$ (176 kg), methylene chloride (474 kg), acetonitrile (340 kg), and triethylsilane (205 kg). The resulting mixture is stirred at 18 to 20° C. for 70 min. After completion of the reaction, water (1263 L) is added at 20 to 30° C. within 1 hr 30 min and the mixture is partially distilled at 30 to 53° C. under atmospheric pressure and the phases are separated. Toluene (698 kg) is added to the organic phase and solvent is distilled off under reduced pressure at 22 to 33° C. The product is then crystallized by addition of seeding crystals (0.5 kg) at 31° C. and water (267 kg) added after cooling to 20° C. The reaction mixture is cooled to 5° C. within 55 min and stirred at 3 to 5° C. for 12 hrs. Finally the product is collected on a centrifuge as colourless, crystalline solid, washed with toluene (348 kg) and dried at 22 to 58° C. 211 kg (73%) of product are obtained. The identity of the product is determined via the HPLC retention time.

Example 5b

Synthesis of the Glucoside II.1

To a solution of the iodide V.1 (30 g) in tetrahydrofuran (55 mL) is added Turbogrignard solution (isopropylmagnesium chloride/lithium chloride solution, 14 weight-% iPrMgCl in THF, molar ratio LiCl:iPrMgCl=0.9-1.1 mol/mol) (53 g) at −14 to −13° C. temperature within 35 min. On completion of the addition the conversion is determined via HPLC analysis. The reaction is regarded as completed when the area of the peak corresponding to the iodide V.1 is smaller than 5.0% of the total area of both peaks, iodide V.1 and the corresponding desiodo compound of iodide V.1. If the reaction is not completed, additional Turbogrignard solution is added until the criterion is met. In this particular case the result is 0.35%. Then the lactone IV.1 (36 g) is added at −15 to −6° C. temperature within 15 min. The resulting mixture is stirred for further 1 hr at −6 to −7° C. On completion, the conversion is determined via HPLC analysis (for information). On completion, a solution of citric acid in water (105 mL; concentration: 10%-weight) is added to the reaction mixture at −15 to 10° C. within 30 min.

The solvent is partially distilled off from the reaction mixture (residual volume: 200 mL) at 20 to 35° C. under reduced pressure and 2-methyltetrahydrofuran (71 mL) is added. Then the mixture is stirred for 25 min at 30° C. Then the stirrer is switched off and the phases are separated at 30° C. After phase separation the pH value of the organic phase is measured with a pH electrode (Mettler Toledo MT HA 405 DPA SC) or alternatively with pH indicator paper (such as pH-Fix 0-14, Macherey and Nagel). The measured pH value is 3. Then solvent is distilled off from the organic phase at 35° C. under reduced pressure and methanol (126 mL) is added followed by the addition of a solution of 1.25N HCl in methanol (10.1 mL) at 25° C. (pH=1-2). Full conversion to the acetale III.1 is achieved by subsequent distillation at 35° C. under reduced pressure and addition of methanol (47 mL).

Completion of the reaction is obtained when two criteria are fulfilled:

1) The ratio of the sum of the HPLC-area of the alpha-form+beta-form of intermediate III.1 relative to the area of intermediate IIIa.1 is greater or equal to 96.0%:4.0%. In this particular case the ratio is 99.6%:0.43%.

2) The ratio of the HPLC-area of the alpha-form of intermediate III.1 to the beta-form of III.1 is greater or equal to 97.0% to 3.0%. In this particular case the ratio is 98.7%:1.3%.

Triethylamin (2.1 mL) is added (pH=9) and solvent is distilled off at 35° C. under reduced pressure, acetonitrile (120 mL) is added and further distilled under reduced pressure at 30 to 35° C. This procedure is repeated (addition of acetonitrile: 102 mL) and methylene chloride (55 mL) is added to the resulting mixture to yield a mixture of the acetale III.1 in acetonitrile and methylene chloride. The water content of the mixture is determined via Karl Fischer titration (result: 0.04%).

The reaction mixture is then added within 1 hr 5 min at 20° C. to a preformed mixture of $AlCl_3$ (19.8 g), methylene chloride (49 mL), acetonitrile (51 mL), and triethylsilane (23 g). The resulting mixture is stirred at 20 to 30° C. for 60 min. After completion of the reaction, water (156 mL) is added at 20° C. within 25 min and the mixture is partially distilled at 55° C. under atmospheric pressure and the phases are separated at 33° C. The mixture is heated to 43° C. and toluene (90 mL) is added and solvent is distilled off under reduced pressure at 41 to 43° C. Then acetonitrile (10 mL) is added at 41° C. and the percentage of acetonitrile is determined via GC measurement. In this particular case, the acetonitrile percentage is 27%-weight. The product is then crystallized by addition of seeding crystals (0.1 g) at 44° C. and the mixture is further stirred at 44° C. for 15 min. The mixture is then cooled to 20° C. within 60 min and water (142 mL) is added at 20° C. within 30 min. The reaction mixture is cooled to 0 to 5° C. within 60 min and stirred at 3° C. for 16 hrs. Finally the product is collected on a filter as colourless, crystalline solid, washed with toluene (80 mL) and dried at 20 to 70° C. 20.4 g (62.6%) of product are obtained. The identity of the product is determined via the HPLC retention time.

Preparation of the Crystalline Form:

Experiment A:

A solution of the compound A (79.0 kg) in a mixture of toluene (186.6 kg) and ethanol (187.2 kg) is heated to reflux until complete dissolution and filtered (hot filtration). The filter is washed with toluene (19.6 kg) and the washing solution is combined with the product solution. The product solution is then cooled to 66° C. and seeding crystals (0.1 kg) are added. The product solution is then cooled to 22° C. using a defined cooling ramp: within 30 min to 57° C., then within 90 min to 50° C., then within 60 min to 41° C., then within 60 min to 22° C. Then the suspension is further stirred at 21° C. for 1 hr, collected on a centrifuge and washed with ethanol (124.8 kg) and dried at about 70° C. 65.5 kg (82.9%) of the product is obtained as white crystals with a HPLC purity of 99.9%.

Via differential scanning calorimetry (DSC) as described hereinbefore, a melting point of 151° C. is determined (FIG. 2).

Via X-ray powder diffraction as described hereinbefore, using $CuK_{\alpha1}$ radiation, the crystalline form is characterised and a pattern as shown in the FIG. 1 is obtained. The intensity shown in the FIG. 1 is given in units of cps (counts per second) and is background corrected.

In addition the crystalline form is characterised by the following lattice parameters: orthorhombic symmetry, space group $P2_12_12_1$ with the cell parameters, a=5.70(1) Å, b=9.25(2) Å, c=39.83(1) Å, and cell volume=2101(1) Å3 which can be obtained by indexing of the X-ray powder diagram to be measured at room temperature using $CuK_{\alpha1}$ radiation, which comprises peaks at degrees 2Θ (±0.1 degrees 2Θ) as contained in Table 1. In the Table 1 above the values "2Θ[°]" denote the angle of diffraction in degrees and the values "d [Å]" denote the specified distances in Å between the lattice planes. Furthermore the h, k, l indices are provided and the difference between the experimental and the calculated d-values in Å.

TABLE 1

Indexed* X-ray powder diffraction pattern of the crystalline form (only peaks up to 30° in 2 Θ are listed):

| 2 Θ [°] | d-value [Å] | Intensity $I/I_0$ [%] | \multicolumn{3}{c}{Indexing} | $d_{exp-calc}$ [Å] |
|---|---|---|---|---|---|---|
| | | | h | k | l | |
| 4.43 | 19.93 | 10 | 0 | 0 | 2 | −0.003 |
| 8.86 | 9.97 | 3 | 0 | 0 | 4 | −0.010 |
| 9.82 | 9.00 | 3 | 0 | 1 | 1 | 0.014 |
| 11.63 | 7.60 | 2 | 0 | 1 | 3 | −0.020 |
| 13.32 | 6.64 | 22 | 0 | 0 | 6 | −0.001 |
| 14.66 | 6.04 | 36 | 0 | 1 | 5 | −0.005 |
| 15.69 | 5.64 | 50 | 1 | 0 | 1 | −0.001 |
| 16.16 | 5.48 | 16 | 1 | 0 | 2 | −0.006 |
| 17.92 | 4.95 | 71 | 1 | 0 | 4 | −0.001 |
| 18.30 | 4.84 | 24 | 0 | 1 | 7 | 0.011 |
| 18.40 | 4.82 | 26 | 1 | 1 | 1 | −0.002 |
| 18.81 | 4.71 | 100 | 1 | 1 | 2 | 0.000 |
| 19.13 | 4.64 | 67 | 1 | 0 | 5 | 0.000 |
| 19.46 | 4.56 | 31 | 1 | 1 | 3 | −0.002 |
| 20.34 | 4.36 | 67 | 1 | 1 | 4 | −0.005 |
| 20.52 | 4.33 | 25 | 1 | 0 | 6 | −0.003 |
| 21.15 | 4.20 | 7 | 0 | 2 | 4 | −0.006 |
| 21.43 | 4.14 | 13 | 1 | 1 | 5 | 0.003 |
| 22.06 | 4.03 | 35 | 1 | 0 | 7 | 0.002 |
| 22.68 | 3.92 | 30 | 1 | 1 | 6 | 0.001 |
| 23.42 | 3.80 | 20 | 0 | 2 | 6 | 0.006 |
| 23.71 | 3.75 | 8 | 1 | 0 | 8 | 0.003 |
| 24.08 | 3.69 | 5 | 1 | 1 | 7 | 0.003 |
| 24.31 | 3.66 | 9 | 0 | 1 | 10 | 0.007 |
| 24.77 | 3.59 | 14 | 1 | 2 | 0 | 0.007 |
| 25.18 | 3.53 | 30 | 1 | 2 | 2 | 0.004 |
| 25.62 | 3.47 | 29 | 1 | 1 | 8 | 0.007 |
| 26.36 | 3.38 | 3 | 1 | 2 | 4 | 0.003 |
| 26.84 | 3.32 | 16 | 0 | 0 | 12 | 0.003 |
| 27.24 | 3.27 | 16 | 1 | 1 | 9 | −0.010 |
| 27.87 | 3.20 | 2 | 0 | 2 | 9 | 0.001 |
| 28.22 | 3.16 | 2 | 1 | 2 | 6 | −0.002 |
| 28.98 | 3.08 | 5 | 1 | 1 | 10 | 0.001 |
| 29.39 | 3.04 | 15 | 1 | 2 | 7 | 0.010 |
| 29.55 | 3.02 | 3 | 0 | 2 | 10 | −0.016 |

*For indexing the lattice parameters from single crystal analysis are used as starting values.

Refined cell parameters from XRPD-pattern:
all peaks (35) up to 30° Θ indexed
symmetry: orthorhombic
space group: $P2_12_12_1$
a=5.70(1) Å
b=9.25(2) Å
c=39.83(1) Å
α=β=γ=90°
V=2101(1) Å$^3$
Figure of merit: 118
Experiment B:
In the following experiment it is investigated how the method according to this invention is able to deplete an impurity of the formula IMP.1 as described hereinbefore.

The compound of the formula IMP.1 is added to the crystalline form of the compound A as obtained according to the Experiment A such that the amounts according to the Table 2 are obtained. For example in order to obtain the 0.5 weight-% mixture 6.96 g of the crystalline form of the compound A as obtained according to the Experiment A and 0.04 g the compound IMP.1 are combined.

Thereafter half of this mixture of compounds is recrystallized according to the procedure of the Experiment A on a laboratory scale. The crystalline form of compound A is obtained as a white crystalline material. The content of the compound of the formula IMP.1 is analyzed via HPLC.

The other half of this mixture of compounds is recrystallized using a mixture of methanol and water according to the following procedure:

About 7 g of a mixture of the crystalline form of the compound A as obtained according to the Experiment A and the compound IMP.1 is added to a mixture of methanol (7.1 g) and water (7.3 g) and is heated to 60° C. until complete dissolution. The clear solution is stirred for 15 min. Then water (11.9 g) is added to the solution and after completion of the addition the solution is cooled to 57° C. and seeding crystals are added. The solution is then further stirred at 57° C. for 30 min. The product solution is then cooled to 25° C. within 2 hrs and 20 min. Then the suspension is further stirred at 25° C. for 15 min, collected on a filter and washed with a mixture of methanol (1.66 g) and water (9.5 g) and dried at about 45° C. 6.5 g (93.1%) of the product is obtained as white crystals.

The compound A is obtained as a white crystalline material. The content of the compound of the formula IMP.1 is analyzed via HPLC.

TABLE 2

Amount of the impurity IMP.1 in the compound A

| Before recrystallization (weight-%) | After recrystallization using toluene/ethanol (HPLC-%) | After recrystallization using methanol/water (HPLC-%) |
|---|---|---|
| 0.5% | 0.07% | 0.07% |
| 1.0% | 0.06% | 0.12% |
| 1.5% | 0.07% | 0.85% |
| 2.0% | 0.09% | 0.67% |
| 3.0% | 0.14% | 1.68% |
| 5.0% | 0.34% | 3.05% |

It is observed that using a crystallization process with a mixture of toluene and ethanol a better depletion of the impurity IMP.1 can be obtained than with a process using a methanol/water mixture.

Experiment C:

In the following experiment it is investigated how the method according to this invention is able to deplete an impurity of the formula IMP.2 as described hereinbefore.

Different samples of raw material of the compound A, for example as obtained from a not optimized lab-scale procedure according to Example 5a or 5b, are analyzed via HPLC with respect to their content of IPM.2.

Thereafter each sample is recrystallized according to the procedure of the Experiment A on a laboratory scale using a mixture of toluene and ethanol to obtain the crystalline form of compound A. The content of IPM.2 and the overall purity of the crystalline form of compound A is analyzed via HPLC.

TABLE 3

| Content of IMP.2 before recrystallization (HPLC-%) | Content of IMP.2 after recrystallization (HPLC-%) | Overall purity after recrystallization using toluene/ethanol (HPLC-%) | Yield |
|---|---|---|---|
| 0.89% | 0.05% | 99.95% | 90.1% |
| 1.26% | 0.14% | 99.86% | 89.3% |
| 1.75% | 0.13% | 99.82% | 87.1% |
| 2.75% | 0.17% | 99.72% | 86.1% |
| 3.94% | 0.29% | 99.61% | 79.1% |
| 7.30% | 0.51% | 99.21% | 73.3% |

Experiment D:

In the following experiment it is investigated how the method according to this invention is able to purify raw material of the compound A.

Different samples of raw material of the compound A, for example as obtained from a not optimized lab-scale procedure according to Example 5a or 5b, are analyzed via HPLC with respect to their purity.

Thereafter each sample is recrystallized according to the procedure of the Experiment A on a laboratory scale using a mixture of toluene and ethanol to obtain the crystalline form of compound A. The overall purity of the crystalline form of compound A is analyzed via HPLC.

The other half of each sample is recrystallized using a mixture of methanol and water according to the procedure as described in the Experiment B.

The purities of the samples of the raw material and the crystallized material are given in the Table 4.

TABLE 4

| Purity before recrystallization (HPLC-%) | Purity after recrystallization using toluene/ethanol (HPLC-%) | Purity after recrystallization using methanol/water (HPLC-%) |
|---|---|---|
| 96.17% | 99.82% | 98.25% |
| 96.74% | 99.84% | 99.64% |
| 97.09% | 99.80% | 99.26% |
| 97.43% | 99.81% | 99.54% |
| 95.60% | 99.75% | 98.63% |

It is observed that using a crystallization process with a mixture of toluene and ethanol a higher purity of the compound A can be obtained than with a process using a methanol/water mixture.

Experiment E:

In the following experiment the influence of the solvent mixture and ratio on the purity and yield of the recrystallization procedure according to Experiment A is investigated.

Therefore, a sample of the of raw material of the compound A, for example as obtained according to Example 5a or 5b, is analyzed via HPLC with respect to its purity and the result is found to be 95.16%. Then, this sample is recrystallized according to the procedure of Experiment A on a laboratory scale (compound A: 35 g; sum of first and second solvent: 162 g) with the modification that the two solvents ethanol and toluene are replaced against the given solvent mixtures in Table 5 to obtain the crystalline form of compound A. The overall purity of the crystalline form of compound A is analyzed via HPLC.

TABLE 5

| Solvent system (ratio weight:weight) | Overall purity after recrystallization (HPLC-%) | Yield |
|---|---|---|
| Ethanol/Toluene = 1:1 | 99.72% | 80.8% |
| 1-Propanol/Toluene = 1:1 | 99.80% | 82.2% |
| 2-Propanol/Toluene = 1:1 | 99.72% | 72.0% |
| Methanol/Toluene = 1:4 | 99.69% | 54.6% |
| Ethanol/Tetrahydrofuran = 4:1 | 99.62% | 82.9% |
| 2-Propanol/Tetrahydrofuran = 2:1 | 99.67% | 67.9% |
| Ethanol/n-Propylacetate = 1:1 | 99.68% | 79.1% |
| Ethanol/Methylethylketone = 1:1 | 99.61% | 67.1% |
| Ethanol/Ethylacetate = 1:1 | 99.70% | 78.4% |

Experiment F:

In the following experiment it is investigated how the method according to this invention is able to purify raw material of the compound A in comparison to a procedure using a mixture of ethanol and water (see for example the experiment "Variant 2" in WO 2006/117359).

A sample of raw material of the compound A, for example as obtained from a not optimized lab-scale procedure according to Example 5a or 5b, is analyzed via HPLC with respect to their purity.

Thereafter the sample is recrystallized according to the procedure of the Experiment A on a laboratory scale using a mixture of toluene and ethanol to obtain the crystalline form of compound A. The overall purity of the crystalline form of compound A is analyzed via HPLC.

The other half of the sample is recrystallized using a mixture of ethanol and water according to the following procedure:

40 g of compound A are dissolved in 200 mL of water/ethanol mixture (2:3 volume ratio) upon heating up to about 50° C. 320 mL of water are added at a temperature range of 45 to 50° C. and the solution is allowed to cool to about 20° C. in 1 to 3 hrs.

After 16 hrs the crystalline form is isolated as beige crystals by filtration. The product is dried at elevated temperature (40 to 50° C.) for about 4 to 6 hrs.

The purities of the samples of the raw material and the crystallized material are given in the Table 6.

TABLE 6

| Purity before recrystallization (HPLC-%) | Purity after recrystallization using toluene/ethanol (HPLC-%) | Purity after recrystallization using ethanol/water (HPLC-%) |
|---|---|---|
| 96.14% | 99.74% | 97.4% |

It is observed that using a crystallization process with a mixture of toluene and ethanol a higher purity of the compound A can be obtained than with a process using an ethanol/water mixture.

The invention claimed is:

1. A method for preparing a crystalline form of a compound 1-chloro-4-(B-D-glucopyranos-1-yl)-2-[4-((S)-tetrahydro-furan-3-yloxy)-benzyl]-benzene comprising the following steps:
    (a) dissolving the compound in a mixture of at least two solvents to form a solution wherein the first solvent is selected from the group of solvents consisting of toluene and tetrahydrofuran, and the second solvent is selected from the group of solvents consisting of methanol, ethanol, 1-propanol and 2-propanol;

(b) storing the solution to precipitate the crystalline form of the compound out of solution;
(c) isolating the crystalline form of the compound from the solution.

2. A method according to the claim 1, wherein the first solvent is toluene.

3. A method according to the claim 2, wherein the second solvent is ethanol, 1-propanol or 2-propanol.

4. A method according to the claim 1, wherein the mixture of at least two solvents is selected from the group of combinations consisting of toluene/ethanol, toluene/1-propanol and toluene/2-propanol.

5. A method according to the claim 1, wherein the crystalline form is characterized by an X-ray powder diffraction pattern that comprises peaks at 18.84, 20.36 and 25.21 degrees 2Θ (±0.1 degrees 2Θ), wherein said X-ray powder diffraction pattern is made using $CuK_{\alpha 1}$ radiation.

6. A method according to the claim 4, wherein the mixture of at least two solvents is the combination consisting of toluene/ethanol.

7. A method according to the claim 4, wherein the weight ratio of the first solvent to the second solvent is in the range from about 1:5 to 5:1.

8. A method according to the claim 4, wherein the weight ratio of the first solvent to the second solvent is in the range from about 1:2 to 2:1.

9. A method according to the claim 1, wherein the mixture of at least two solvents is selected from the group of combinations consisting of tetrahydrofuran/ethanol, tetrahydrofuran/1-propanol and tetrahydrofuran/2-propanol.

10. A method according to the claim 9, wherein the weight ratio of the first solvent to the second solvent is in the range from about 1:10 to 2:1.

11. A method according to the claim 9, wherein the weight ratio of the first solvent to the second solvent is in the range from about 1:5 to 1:1.

12. A method according to the claim 9, wherein the weight ratio of the first solvent to the second solvent is in the range from about 1:4 to 1:2.

13. A method according to claim 5, wherein the X-ray powder diffraction pattern further comprises peaks at 14.69, 19.16 and 19.50 degrees 2Θ (±0.1 degrees 2Θ), wherein said X-ray powder diffraction pattern is made using $CuK_{\alpha 1}$ radiation.

* * * * *